United States Patent [19]

Barberet et al.

[11] Patent Number: Plant 6,272

[45] Date of Patent: Sep. 6, 1988

[54] CARNATION NAMED 'LONKINDAL'

[75] Inventors: Nicole Barberet; Yves Ducloux, both of Antibes, France

[73] Assignee: Laboratoire de Physiologie Vegetale de la Londe, La Londe, France

[21] Appl. No.: 906,540

[22] Filed: Sep. 12, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of spray carnation having small brilliant white blooms produced profusely at intermittent intervals of spring, midseason and fall, appearing in clusters at the upper portion of strong, moderately branched, erect stem, the flowers being distinguished by the brilliant white color of the petals and the plant itself being distinguished by its very tall growth and vigorous, upright and rigid habit with abundant foliage.

1 Drawing Sheet

BACKGROUND OF THE NEW PLANT

This new carnation cultivar originated at La Londe, Les Maures, France, as a sport of a patented carnation named "Longorin" (U.S. Plant Pat. No. 5,628) being grown in our greenhouses for the production of cut flowers, as well as for propagation and sale of plants to commercial growers for spray carnation uses. This sport was discovered by us in our greenhouse at La Londe in 1983. This plant was reproduced by cuttings with very good results so that further propagation was directed to be carried on through a series of successive generations by means of cuttings from previous plants produced in the same manner. This extended propagation of our new plant demonstrated clearly that the novel characteristics of its blooming and growth habits would remain true from generation to generation and appeared to be firmly fixed.

DESCRIPTION OF THE DRAWING

Our new variety of spray carnation is illustrated by the accompanying photographic drawing, which shows in full color the upper portion of a typical spray stem bearing buds and flowers at various stages of growth, the colors shown being as nearly true to those specified as is reasonably possible to obtain by conventional photographic procedures.

DESCRIPTION OF THE NEW PLANT

The following is a detailed description of our new carnation plant based upon observations of greenhouse plants grown at La Londe, Les Maures, France, in the spring of the year, the color designations being accordinug to the R.H.S. Colour Chart published by The Royal Horticultural Society of London, England.

THE PLANT

Origin: Sport.
Parentage: Longorin (U.S. Plant Pat. No. 5,628).
Classification:
- *Botanic.*—*Dianthus caryophyllus.*
- *Commercial.*—Spray carnation.

Form: Bush of tall spray shape comprising at least four stems emitted from the main stem near the ground.
Main stem:
- *Length.*—Less than about 15 cm. due to pinching.

Branching character: Moderately branched.

Growth: Vigorous, upright and rigid.
Foliage:
- *Quantity.*—Rather abundant.
- *Number of leaves.*—More than 120.
- *Size of leaf.*—Leaf averages about 10 cm. long and 0.8 cm. wide at the seventh node.
- *Leaf shape.*—Long with sharp point and rolled margins.
- *Texture.*—Leathery.
- *Color.*—Both upper and lower sides, 189A.
- *Leaflets.*—None.
- *Ribs, veins and rachis.*—Hardly noticeable.

THE BUD

Size: Small
- *Diameter.*—Averages 1.2 cm.
- *Length.*—Averages about 2.5 cm.

Shape: Ovoid.
Rate of opening: Normal for carnations.
Color of petals:
- *When sepals first divide.*—155B.
- *When petals begin to unfurl.*—155B.

Sepals:
- *Number.*—5 to 6.
- *Shape.*—Joined together at lower part with the upper part somewhat oval in shape and having a sharp, pointed apex. The sepals are hooded over the bud before dividing and continue to stand up as the flower opens.
- *Color.*—Both outer and inner petals: Body — 155B. Base — Greenish. Reverse side — 155B.

Petaloids: Less than 5.
- *Size.*—Smaller than petals.
- *Color.*—Same as petals.

Flower stem:
- *Length.*—Averaging about 68 cm. (cut at tenth node).
- *Character.*—Strong and upright.
- *Color.*—189B.

Discoloration after full bloom: None.
Fragrance: Lightly perceptible.
Persistence: The flowers hang on and dry.
Lasting quality:
- *As a cut flower.*—At least ten days in vase keeping.

Disease resistence: Resistent to *Fusarium oxysporum* at La Londe, Les Maures, France.

REPRODUCTIVE ORGANS

Stamens:
*Number.*—1 to 3.
*Arrangement.*—Around the ovary.
*Anthers.*—Size: Less than 4 mm. Color: White.
Filaments:
*Length.*—Averages about 2.5 cm.
*Color.*—White.
*Color.*—Inside — 145D. Outside — 137D and 145B.
*Striae.*—Longitudinal.
Calyx: Long and of cylindrical shape.
*Aspect.*—Smooth; the calyx does not split.
Flower stem:
*Length.*—About 68 cm., in average.
*Character.*—Erect and rather thin.
*Color.*—189A.

THE FLOWER

Blooming habit: Recurrent, blooming profusely during spring, midseason and fall blooming periods with a tendency to give fewer blooms in the fall.
Size of bloom: Small.
*Diameter.*—Averaging about 4.6 cm.
*Depth.*—Averaging about 4.7 cm.
Borne: As a cluster.
Shape:
*When bloom first opens.*—High centered.
*When bloom matures.*—Dome shaped.
Petalage:

*Number of petals.*—About 22, in average.
*Arrangement.*—Generally imbricated.
*Petal form.*—Fan shaped with wavy edges, a rounded apex and flat at the center.
*Texture.*—Leathery.
*Appearance.*—Satiny.
Pistils:
*Number.*—2.
Styles:
*Length.*—Averaging about 2.5 cm.
*Color.*—White.
Stigmas:
*Color.*—White.
Ovaries: The ovaries are ribbed.

This new spray carnation variety most nearly resembles the variety 'Longorin' (U.S. Plant Pat. No. 5,628) but differs from that variety by color. It also nearly resembles the variety again of 'Lonblitec' (U.S. Plant Pat. No. 5,434) but differs from that variety because of its smaller flower and its resistance to *Fusarium oxysporum.*

We claim:

1. The new and distinct variety of spray carnation, substantially as herein shown and described, characterized by its intermittent flowering habit with profuse production of moderately branched flowers having a brilliant white coloration, supported by erect, thin peduncles averaging 68 cm. in length and having a rapid, vigorous and upright growth habit.

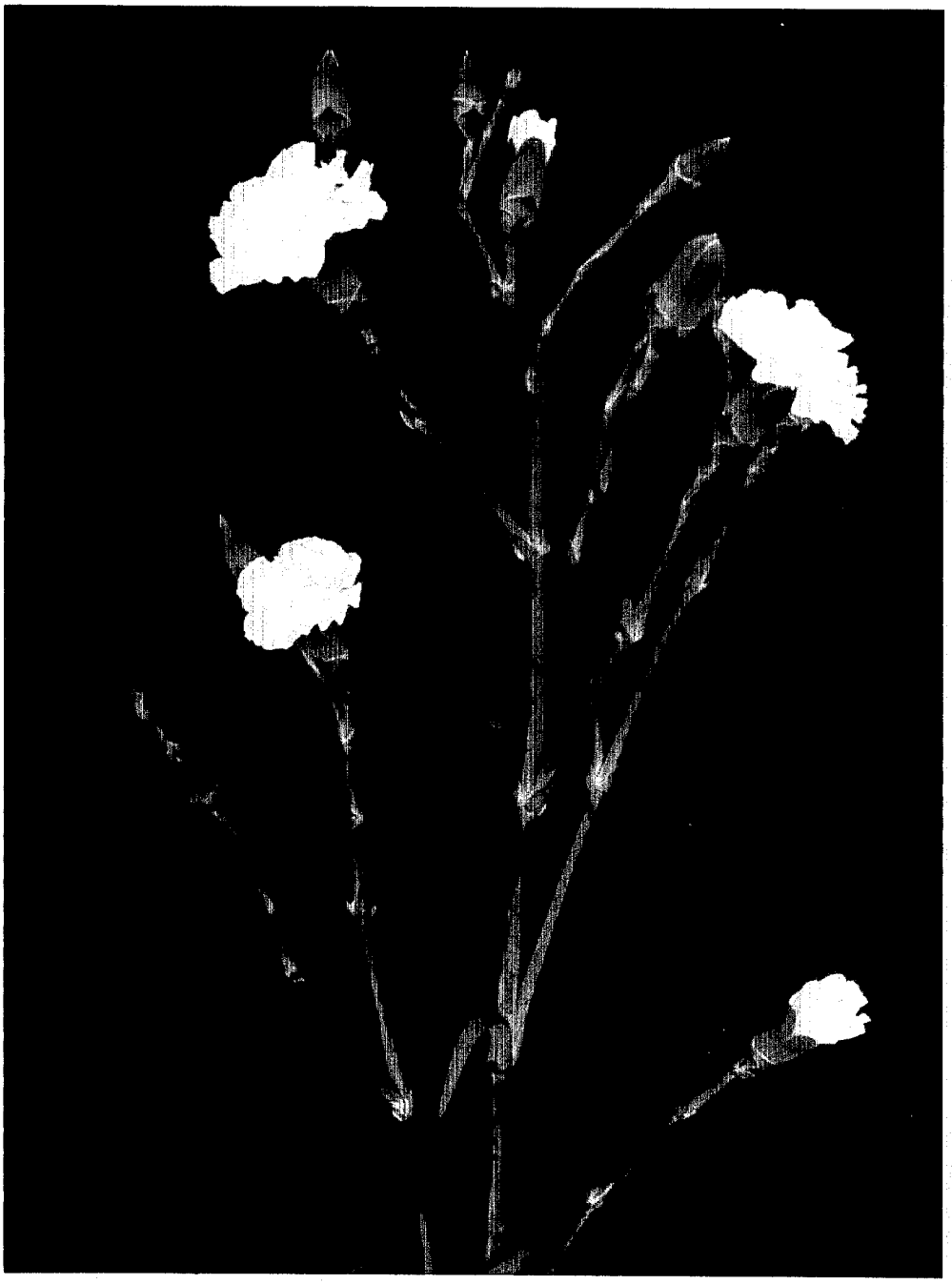

* * * * *